United States Patent [19]

Di Pietro et al.

[11] 4,303,675
[45] Dec. 1, 1981

[54] MOSQUITO REPELLENT

[75] Inventors: Joseph Di Pietro; Giovanni Celia, both of San Donato Milanese, Italy

[73] Assignee: Anic, S.p.A., Palermo, Italy

[21] Appl. No.: 119,976

[22] Filed: Feb. 8, 1980

Related U.S. Application Data

[63] Continuation of Ser. No. 941,375, Sep. 12, 1978, abandoned.

[30] Foreign Application Priority Data

Sep. 21, 1977 [IT] Italy .................................. 27751 A/77

[51] Int. Cl.$^3$ ............................................. A01N 31/00
[52] U.S. Cl. ............................ 424/343; 424/DIG. 10
[58] Field of Search ........................ 424/343, DIG. 10

[56] References Cited

U.S. PATENT DOCUMENTS 2,465,470  3/1949  Omohundro et al. ...... 424/DIG. 10

OTHER PUBLICATIONS

Chem. Abst. vol. 56 (1962), p. 11445i–11446a.
Roth et al., USDA–Ag. Research Service, "Tests of Repellents Against Tabanids", ARS-33-2, Sep. 1954.
King; Chem. Evaluated as Insecticides & Repellents at Orlando, Fla., May 1954, pp. 12–16 & 188–189.
Agriculture Handbook No. 340; Materials Evaluated as Insecticides, Repellents, and Chemosterilants, at Orlando & Gainesville, Fla., Aug. 1967. pp. 7–10 & 194.

*Primary Examiner*—Allen J. Robinson
*Attorney, Agent, or Firm*—Morgan, Finnegan, Pine, Foley & Lee

[57] ABSTRACT

2,5-dimethyl-2,5-hexanediol has proven to be an efficient mosquito repellent which has a persistent action and is water soluble.

Repellency tests are reported and discussed.

3 Claims, No Drawings

MOSQUITO REPELLENT

This is a continuation of application Ser. No. 941,375, filed Sept. 12, 1978, now abandoned.

This invention relates to a novel repellent agent for mosquitoes based on 2,5-dimethyl-2,5 hexanediol.

For protecting humans against insects, which are often a vehicle of infection or diseases with their stings, a number of products have been prepared which exert on insects different actions such as actions which cause the insect death with different mechanisms, or which alter the reproductive functions of insects, or which alter the insect sensorial system, thus modifying their sense of orientation.

The agents which exert the last cited action are indicated as "repellents" and are used more particularly for protection against mosquitoes: these insects find the food-stuffs for ripening their eggs ready for reproduction in the blood of warm-blood animals.

The so-called repellents, by virtue of a mechanism which has not yet been fully elucidated, prevent the mosquitoes from tracking the emanations of heat and moisture delivered by the skin of men and warm-blood animals and thus cause the mosquito flight to swerve, inasmuch as the mosquito flight is much more sensorial than visual.

The compounds of usual employment are used in the form of creams, lotions, sprays or soaking agents for towels, thermal diffusion tabloids and thus generally contain the repellent agent proper united with solvents, bustrates or inert vehicles of any kind. They are spread onto the exposed skin which, during a certain time, is not exposed to insect attacks, no detrimental effects being experienced for the skin or the system, or they are caused to vaporize in the ambient atmosphere due to thermal effect.

There have been tested, for repellency, a number of compounds even though there were no clear ideas on the correlations existing between the repellency action and the chemical nature and structure of the compounds concerned.

It has merely been established that the mol wt of the repellent compounds is preferably comprised between 150 and 250 and that the form of the molecule has a certain importance. As a matter of fact, planar molecules are poorly repellent, whereas bulky molecules (the comparison has been made on isomers, such as dimethyl phthalate and dimethyl terephthalate) exhibit a greater repellent power. See the article by R. H. Wright Why Mosquito-repellents repel—Scientific American, July 1975.

It has now been found, during progress of tests for the exploitation of 2,5-dimethyl-2,5 -hexanediol, and this is the subject matter of this invention, that 2,5-dimethyl-2,5-hexanediol by itself, even having a mol wt lower than that which is regarded as an optimum (146) exhibits an excellent repellent action towards mosquitoes.

Its action is long lasting and can be compared with that of the principal agents which have been found to have a repellent action and with that of those usually adopted (This is surprising since a similar compound, 1,6-hexanediol is described in the cited article as a poor repellent).

In addition, and this is quite an asset, 2,5-dimethyl-2,5-hexanediol is water soluble so that it can be formulated for being used in an aqueous medium, which is a positive factor both from the economical point of view and from that of practical use.

Water, in fact, has no side effects on skin or in general on the organisms with which it comes into contact.

For the purpose of illustration without limitation, the tests which have been performed are described herein in comparison with like tests carried out on diethyltoluamide, which is the base of the present commercial repellents.

The concentration of the solutions used is not particularly critical since after the evaporation of the solvent, a protective layer is left, which repels mosquitoes.

At any rate, solutions with concentrations up to 30% can be employed.

For the tests in question, there have been adopted 10% solutions in comparison with the same concentrations of the comparison repellent agent.

For testing purposes, a cage with transparent walls has been used, holding mosquitoes of the genus Aedes Aegypti (yellow fever mosquitoes): in the cage there were placed two confrontingly arranged wood tablets (28.5×5×1 centimeter): one tablet was spread with the solution containing the product to be tested and the other, the control, with the solvent for the product. The cage was shaken so as to stimulate mosquito flight and after one minute there was observed the number of insects which lay on each tablet.

To offset any effects possibly due to the position of the tablets, these were shifted every three readings.

The tests have been repeated with the same procedure using N-diethyltoluamide dissolved in acetone (it is not water soluble).

The results of testing are tabulated in TABLES 1 and 2.

TABLE 1

RESULTS OBTAINED WITH 2,5-DIMETHYL-2,5-HEXANE-DIOL DISSOLVED IN TAP WATER - CONCENTRATION 10% -

| Test No | Control wood tablet No mosquitoes | Treated wood tablet No mosquitoes |
|---|---|---|
| 1 | 7 | 1* |
| 2 | 6 | 0 |
| 3 | 3 | 0 |
| 4 | 5 | 0 |
| 5 | 3 | 0 |
| 6 | 2 | 0 |
| 7 | 1 | 0 |
| 8 | 4 | 0 |
| 9 | 6 | 0 |
| 10 | 10 | 1 |
| 11 | 7 | 0 |
| 12 | 2 | 0 |
| 13 | 3 | 0 |
| 14 | 4 | 0 |
| 15 | 6 | 0 |
| 16 | 9 | 0 |
| 17 | 8 | 0 |
| 18 | 7 | 0 |
| 19 | 7 | 0 |
| 20 | 5 | 0 |
| 21 | 7 | 0 |
| 22 | 5 | 0 |
| 23 | 10 | 0 |
| 24 | 5 | 0 |
| 25 | 10 | 0 |
| 26 | 7 | 0 |
| 27 | 5 | 0 |

*The numbers with asterisk indicate the mosquitoes which lit and flew away a few second later.

TABLE 2

RESULTS OBTAINED WITH N-DIETHYLTOLUAMIDE DISSOLVED IN ACETONE - CONCENTRATION 10% -

| Test No | Control wood tablet No mosquitoes | Treated wood tablet No mosquitoes |
| --- | --- | --- |
| 1 | 4 | 0 |
| 2 | 4 | 0 |
| 3 | 8 | 0 |
| 4 | 6 | 0 |
| 5 | 5 | 1 |
| 6 | 6 | 0 |
| 7 | 4 | 0 |
| 8 | 6 | 0 |
| 9 | 6 | 0 |
| 10 | 7 | 0 |
| 11 | 7 | 0 |
| 12 | 8 | 0 |
| 13 | 5 | 0 |

No decrease of the efficiency of 2,5-dimethyl-2,5-hexanediol has been experienced after one hour and forty minutes.

There have been performed also "in vivo" tests with 2,5-dimethyl-2,5-hexanediol with volunteers by treatment of the arm skin.

In a set of 3-minute exposure no mosquito lit on the treated arms.

The skin of the arms thus treated did not show any alteration of any kind, neither immediately nor subsequently.

We claim:

1. A method of repelling mosquitoes comprising administering a mosquito repelling effective amount of a composition consisting essentially of 2,5-dimethyl-2,5-hexanediol and an inert carrier to a surface to be protected.

2. The method of claim 1 further comprising administering said composition in the form of a cream, lotion, spray, soaking agent for towels, and a thermal diffusion tabloid.

3. The method of claim 1 wherein said surface is the skin of a warm-blooded animal.

* * * * *